United States Patent [19]

Aboud

[11] Patent Number: 5,489,433
[45] Date of Patent: Feb. 6, 1996

[54] ENVIRONMENTALLY SAFE INSECTICIDE

[75] Inventor: George M. Aboud, Phoenix, Ariz.

[73] Assignee: Safe-Tee Chemical Products Company, Phoenix, Ariz.

[21] Appl. No.: 245,743

[22] Filed: May 16, 1994

Related U.S. Application Data

[63] Continuation-in-part of Ser. No. 34,150, Mar. 22, 1993, abandoned, which is a continuation of Ser. No. 638,175, Jan. 4, 1991, abandoned.

[51] Int. Cl.$^6$ .............................. A61K 29/02; A61K 9/10
[52] U.S. Cl. ..................... 424/405; 424/43; 424/406; 424/DIG. 10; 514/937; 514/578; 514/919
[58] Field of Search ...................... 424/405, 406, 424/450, 45, 43; 514/937, 578, 919

[56] References Cited

U.S. PATENT DOCUMENTS

| | | | |
|---|---|---|---|
| 3,624,198 | 11/1971 | Arbaugh | 424/405 |
| 4,581,378 | 4/1986 | Lazar et al. | 424/405 |
| 5,120,716 | 6/1992 | Miyazawa et al. | 514/23 |
| 5,221,535 | 6/1993 | Domb | 424/450 |
| 5,298,250 | 3/1994 | Lett et al. | 424/405 |
| 5,298,525 | 3/1994 | Evers | 424/405 |
| 5,364,626 | 11/1994 | Hasegawa et al. | 424/403 |

*Primary Examiner*—Raj Bawa
*Attorney, Agent, or Firm*—Ogram & Teplitz

[57] ABSTRACT

An environmentally-safe, broad spectrum insecticide that is toxic to invertebrate animals and non-toxic to vertebrate animals. The insecticide comprises a water solution of hydroxy acyclic acid, such as citric acid, and ionic or non-ionic surfactant thoroughly mixed together. The insecticide may be applied by aerosol, misting, spraying, or pouring on the insects or into their abodes. The composition is also an effective mosquito repellant when applied to human skin.

21 Claims, No Drawings

ENVIRONMENTALLY SAFE INSECTICIDE

This is a continuation-in-part of application Ser. No. 8/034,150, filed Mar. 22, 1993, now abandoned which in turn is a continuation of application Ser. No. 07/638,175, filed Jan. 4, 1991, now abandoned.

BACKGROUND OF THE INVENTION

The present invention relates generally to an environmentally safe insecticide and more particularly to novel compositions which are safe for both plant life and vertebrates in general, including human beings, but which are toxic to invertebrate pests such as insects. The composition has the further unexpected benefit of repelling mosquitoes when applied to human skin.

Heretofore, insecticides used for chemically controlling insect infestation fell into five major categories namely, chlorinated hydrocarbons such as LINDANE, METHOXYCHLOR, and the like; organophosphates such as MALATHION, DIBROM, DIAZINON, PHOSPHAMIDON and the like; carbonate compounds such as BAYGON, SEVIN and the like; inorganic compounds such as, arsenic, sulphur, borax, and the like; and botanical compounds such as pyrethrin, strychnine, nicotine, and the like.

The prior chemical insecticides, excluding the botanical compounds, possess several disadvantages. Most of them are highly toxic to fish, wildlife and humans and must be used with caution. Further, the active ingredients are generally not naturally occurring biological constituents and, as such, tend to persist for long lengths of time after their initial application. Consider, for example, the chlorinated hydrocarbons (Petrochemical hydrocarbons are suspect carcinogenic agents) which because of their persistence have been shown to pass through the animal food chain and cause egg shell thinning and egg breakage in many species of birds.

Besides their initial toxic effect, these compounds have sub-acute effects on non-target fauna and flora thereby causing biochemical, behavioral and physiological changes as well as reproductive failure. Furthermore, their adverse effect on the environment in general is widely known and needs no elaboration here.

The ideal insecticide is one that adversely affects only the target species, sublimates without residue when desired, and has no negative environmental effects. As usual, the ideal is a potentially unattainable goal which, nonetheless, is worth striving for.

The desiratum of the present invention was to locate and identify a substance or substances naturally occurring in some part of the environment, which has positive effects, or is at least neutral, upon all fauna and flora other than the targeted pests and is especially lethal upon those pests. Such a substance must also be free of metabolites or breakdown components which themselves are toxic or cause environmental harm. The search for such a substance has been ongoing. To date, however, this search has discovered no alternatives which are truly satisfactory.

One prior art effort to create a non-toxic insecticide used for controlling insect infestation is based on using a non-toxic carrier such as diatomaceous earth which is thoroughly laced with a bait substance such as cane molasses, cane sugar, dextrin, and the like and which after ingestion mechanically kills the insects by lacerating the body and causing the loss of vital fluids. However, such an insecticide poses a threat to non-targeted life and as such does not attain the aforestated desiratum.

BRIEF SUMMARY OF THE INVENTION

The present invention relates generally to a new and novel environmentally safe insecticide which is toxic to invertebrate animals such as insects but which is completely harmless, in the concentrations of usage required, to vertebrates, that is, animals with spines. Surprisingly, the essential active ingredient of the insecticide is present in every living plant and animal. Yet it was discovered that when an excess of the active ingredient is delivered to an insect, it can disrupt the nervous system of the insect which, in turn, causes respiratory failure and death.

The essential ingredients of the present invention are a hydroxy acyclic acid selected from the group consisting of citric, lactic, tartaric, malic, glycolic (gallic), tannic or ascorbic acid, and an ionic or non-ionic surfactant. The purpose of the surfactant is to reduce the surface tension of the insecticidal composition, so that when such composition is applied to the body of an insect, the penetration of the hydroxy acyclic acid into the insect's nervous system is facilitated so as to disrupt the normal respiratory function of the insect and thereby suffocate it.

The insecticide is formed by mixing a dry anhydrous acid with tap water and adding the surfactant thereto. The solution will generally contain up to about 10.5 ounces of the hydroxy acyclic acid and up to about 60 ml of the surfactant per liter of water.

The solution thus prepared and mixed can be applied using conventional delivery techniques such as with an aerosol dispenser or it can be deposited directly upon suspected insect infestation or burrowing sites as by misting, spraying or pouring.

Accordingly, a prime object of the present invention is to provide a new and useful insecticide which is environmentally safe but is selectively toxic to invertebrate animals.

Another object of the present invention is to provide a new and useful insecticide containing hydroxy acyclic acids and an ionic or non-ionic surfactant as its essential active ingredients and which is effective to destroy insects but possess no deleterious action on surrounding flora and fauna.

These and still further objects as shall hereinafter appear are readily fulfilled by the present invention in a remarkably unexpected manner as will be readily discerned from the following detailed description of an exemplary embodiment thereof.

DESCRIPTION OF PREFERRED EMBODIMENTS

The present invention relates to a new and novel environmentally safe insecticide which is toxic to invertebrate animals such as insects but which is otherwise harmless.

This invention is predicated on the use of a composition containing hydroxy acid belonging to the acyclic family of compounds and an ionic or non-ionic surfactant. The specific hydroxy acid used to exemplify this invention is citric acid (2-hydroxy-1,2,3,-propanetricarboxylic acid) $HOOCCH_2C(OHCOOH)CH_2COOH \cdot H_2O$, although lactic, tartaric, malic, glycolic (gallic), tannic, and ascorbic acid, the so-called "food acids", can be substituted therefor with equally favorable results.

Any ionic or non-ionic surfactant may be used together with the hydroxy acyclic acid in formulating the insecticidal composition of the present invention. Suitable surfactants include any of the following conventional surfactant types:

(a) alcohols;
(b) alkanolamides;
(c) alkoxylated derivatives of alcohols, alkyl phenols, amines, amides, fatty acids, fatty esters and oils;
(d) amine acetates and oxides;
(e) aryl, alkyl, aralkyl and alkaryl sulfonates and sulfates;
(f) betaine derivatives;
(g) carboxylated alcohol ethoxylates;
(h) esters of fatty acids, glycols, glycerols, sucrose, glucose and phosporic acid;
(i) fluorcarbon-based surfactants;
(j) imidazolines, imadazolines and other heterocylic surfactants;
(k) isethionates;
(l) lanolin-based derivatives;
(m) lecithin and lecithin derivatives;
(n) lignin and lignin derivatives;
(o) polysaccharides, polyacrylates, polyacrylamides, and other polymeric and block polymeric surfactants;
(p) protein-based surfactants;
(q) quaternary surfactants;
(r) sarcosine derivatives;
(s) silicone-based surfactants;
(t) soaps;
(u) sorbitan derivatives;
(v) sulfates and sulfonates of amines, amides, olefins, petroleum, oils, fatty acids, fatty esters, ethoxylated alcohols and ethoxylated alkyl phenols;
(w) sulfosuccinates and sulfosuccinamates;
(x) taurates; and
(y) thio, mercapto and phosphorous derivatives.

Preferable surfactants include alkaryl polyethylene glycols, alkyl polyethylene glycols, salts of dodecylated oxydibenzene disulfonate, ethoxylated nonylphenol surfactants, aliphatic polyoxyethylene ether surfactants, polyoxyethylene alkyl ether surfactants, and castor oil derivatives.

In formulating the insecticidal composition of the present invention, up to about 10.5 ounces of the hydroxy acyclic acid is mixed into one (1) liter of tap water, and thereafter up to about 60 ml of the surfactant is added into the solution. The optimum amounts of these two components will vary within these broad limits, depending upon the specific hydroxy acyclic acid and surfactant employed. When using citric acid and one of the surfactants listed above as preferred, typical formulations will contain from about 1.5 to about 6.5 ounces, preferably from about 1.5 to about 2.5 ounces, of the citric acid, and from about 1 to about 10 ml, preferably from about 4 to about 6 ml, of the surfactant per liter of water.

The insecticide is applied by any suitable means i.e. aerosol, misting, spraying or pouring down into insect mounds or on to insect nests.

The formulation as described above is environmentally safe, since all fauna and flora contain citric acid in their cells, that is, citric acid (and other food acids) is a natural biological constituent. The insecticide function of the substance occurs in non-vertebrate animals when an excess of the acyclic hydroxy acid such as citric acid is administered thereto. Respiratory failure results in the insect because the normal nervous system rhythm is disrupted by the insecticide. Of particular value is the fact that any excess insecticide (acid base) which falls on alkali soil will self-neutralize itself and be used by the surrounding plants. Likewise, excess insecticide will also remain on acid soil as a residual and eventually be used by the surrounding plants.

The insecticide of the present invention totally eliminates the use of petro and chlorinated solvents for insect control and thereby precludes the contamination of ground water, streams, and air with these environmentally hostile compounds.

It is further noteworthy that the hydroxy acyclic acids, such as citric acid, are hydroscopic, that is, after application, when the water evaporates therefrom, the residue of the insecticide continues to draw insects. Since citric acid is derived by mold fermentation of lemons, limes, pineapple juice, molasses, and the like, it is a natural bait for insects. Upon the occurrence of high humidity or rain fall, the insecticide when disposed on a hard surface, will rehydrate itself.

A further advantage arises when citric acid is the active ingredient in this insecticide, in that it is not only safe for humans but because it is consumed by humans regularly in the form of oranges, lemons, lime juice, tomatoes, and juice-flavoring extracts, confections, soft drinks, medicines, and is used as an antioxidant in many foods.

The insecticide of the present invention, has been extensively tested and found effective in the elimination of regular ants, fireants, cockroaches including both German and the big sewer variety, mosquitoes, locusts, flies, crickets, grasshoppers, tomato worms, beetles, spiders, earwigs (dermaterpa), wasps, hornets, and yellow jackets.

This invention has applicability for residential, industrial and agricultural use.

To assist in the understanding of the present invention and not by way of limitation, the following examples are presented:

EXAMPLE I

To one liter of tap water, 2.1 ounces of citric acid are mixed with stirring to assure uniform dispersion of the acid throughout the water. To the diluted acid-water mixture, 5 ml of alkyl polyethylene glycol (available from Union Carbide under the brand name TERGITOL-TMN) is added with additional stirring to complete the formulation of an environmentally safe insecticide embodying the present invention.

EXAMPLE II

The procedure of Example I was repeated using sodium salt of dodecylated oxydibenzene disulfonate (available from Dow Chemical under the brand name BENAX 2AI) as surfactant to create an environmentally safe insecticide embodying the present invention.

EXAMPLE III

The procedure of Example I was repeated using an ethoxylated nonylphenol surfactant (available from Monsanto Company under the brand name STEROX-N) as the surfactant.

EXAMPLE IV

The preparation prepared according to Example I was placed in a spray bottle and sprayed over a nest of approximately 15 sewer cockroaches. After twenty seconds, all of the roaches were dead.

EXAMPLE V

A preparation prepared according to Example II was loaded in an atomizer and sprayed upon a nest of wasps and after ten seconds, all of the wasps were dead.

EXAMPLE VI

A preparation prepared according to Example III was placed in a pump bottle and sprayed at a swarm of mosquitoes. All of the mosquitoes died within five seconds.

A number of commercially available ionic or non-ionic surfactants can be used to prepare the present invention including alkylaryl polyethylene glycol and alkyl polyethylene glycol (available from Union Carbide under the brand name TERGITOL), the sodium salt of dodecylated oxydibenzene disulfonate (BENAX 2AI Dow); ethoxylated nonylphenol surfactants, aliphatic polyoxyethylene ether, and polyoxyethylene alkyl ether (STEROX, Monsanto); and various castor oil derivatives (SURFACTOL 13, Baker Castor Oil Co.).

Further various of the known so-called "food acids" can be used in place of the citric acid without significantly diminishing the effectiveness of the insecticide. Thus, lactic, tartaric, malic, glycolic, gallic, tannic or ascorbic acid can be substituted for the citric acid specified herein.

A further benefit of the present invention arises from its unexpected properties as an insect repellant when applied to human skin.

From the foregoing, it is readily apparent that a useful embodiment of the present invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

What is claimed is:

1. An environmentally safe insecticide which is non-toxic to vertebrates, consisting essentially of an hydroxy acyclic acid, an ionic or non-ionic surfactant, and water, the amount of said hydroxy acyclic acid being up to about 10.5 ounces per liter of water, the amount of said surfactant being up to about 60 ml per liter of water, said hydroxy acylic acid being selected from the group consisting of citric, lactic, tartaric, malic, glycolic, tannic and ascorbic acids, said surfactant being selected from the group consisting of:

(a) alcohols;
   (b) alkanolamides;
   (c) alkoxylated derivatives of alcohols, alkyl phenols, amines, amides, fatty acids, fatty esters and oils;
   (d) amine acetates and oxides;
   (e) aryl, alkyl, aralkyl and alkaryl sulfonates and sulfates;
   (f) betaine derivatives;
   (g) carboxylated alcohol ethoxylates;
   (h) esters of fatty acids, glycols, glycerols, sucrose, glucose and phosporic acid;
   (i) fluorcarbon-based surfactants;
   (j) imidazolines, imadazolines and other heterocylic surfactants;
   (k) isethionates;
   (l) lanolin-based derivatives;
   (m) lecithin and lecithin derivatives;
   (n) lignin and lignin derivatives;
   (o) polysaccharides, polyacrylates, polyacrylamides, and other polymeric and block polymeric surfactants;
   (p) protein-based surfactants;
   (q) quaternary surfactants;
   (r) sarcosine derivatives;
   (s) silicone-based surfactants;
   (t) soaps;
   (u) sorbitan derivatives;
   (v) sulfates and sulfonates of amines, amides, olefins, petroleum, oils, fatty acids, fatty esters, ethoxylated alcohols and ethoxylated alkyl phenols;
   (w) sulfosuccinates and sulfosuccinamates;
   (x) taurates; and
   (y) thio, mercapto and phosphorous derivatives.

2. The insecticide of claim 1, wherein said hydroxy acyclic acid is citric acid.

3. The insecticide of claim 1, wherein said surfactant is selected from the group consisting of alkaryl polyethylene glycols, alkyl polyethylene glycols, salts of dodecylated oxydibenzene disulfonate, ethoxylated nonylphenol surfactants, aliphatic polyoxyethylene ether surfactants, polyoxyethylene alkyl ether surfactants, and castor oil derivatives.

4. The insecticide of claim 1, wherein the amount of said hydroxy acyclic acid is from about 1.5 to about 6.5 ounces per liter of water.

5. The insecticide of claim 4, wherein the amount of said hydroxy acyclic acid is from about 1.5 to about 2.5 ounces per liter of water.

6. The insecticide of claim 1, wherein the amount of said surfactant is from about 1 to about 10 ml per liter of water.

7. The insecticide of claim 6, wherein the amount of said surfactant is from about 4 to about 6 ml per liter of water.

8. A method of killing insects comprising applying to said insects or to a target site of insect infestation an environmentally safe insecticide which is non-toxic to vertebrates and which consists essentially of an hydroxy acyclic acid, an ionic or non-ionic surfactant, and water, the amount of said hydroxy acyclic acid being up to about 10.5 ounces per liter of water, the amount of said surfactant being up to about 60 ml per liter of water, said hydroxy acylic acid being selected from the group consisting of citric, lactic, tartaric, malic, glycolic, tannic and ascorbic acids, said surfactant being selected from the group consisting of:

(a) alcohols;
   (b) alkanolamides;
   (c) alkoxylated derivatives of alcohols, alkyl phenols, amines, amides, fatty acids, fatty esters and oils;
   (d) amine acetates and oxides;
   (e) aryl, alkyl, aralkyl and alkaryl sulfonates and sulfates;
   (f) betaine derivatives;
   (g) carboxylated alcohol ethoxylates;
   (h) esters of fatty acids, glycols, glycerols, sucrose, glucose and phosporic acid;
   (i) fluorcarbon-based surfactants;
   (j) imidazolines, imadazolines and other heterocylic surfactants;
   (k) isethionates;
   (l) lanolin-based derivatives;
   (m) lecithin and lecithin derivatives;
   (n) lignin and lignin derivatives;
   (o) polysaccharides, polyacrylates, polyacrylamides, and other polymeric and block polymeric surfactants;

(p) protein-based surfactants;

(q) quaternary surfactants;

(r) sarcosine derivatives;

(s) silicone-based surfactants;

(t) soaps;

(u) sorbitan derivatives;

(v) sulfates and sulfonates of amines, amides, olefins, petroleum, oils, fatty acids, fatty esters, ethoxylated alcohols and ethoxylated alkyl phenols;

(w) sulfosuccinates and sulfosuccinamates;

(x) taurates; and (y) thio, mercapto and phosphorous derivatives.

9. The method of claim 8, wherein said hydroxy acyclic acid is citric acid.

10. The method of claim 8, wherein said surfactant is selected from the group consisting of alkaryl polyethylene glycols, alkyl polyethylene glycols, salts of dodecylated oxydibenzene disulfonate, ethoxylated nonylphenol surfactants, aliphatic polyoxyethylene ether surfactants, polyoxyethylene alkyl ether surfactants, and castor oil derivatives.

11. The method of claim 8, wherein the amount of said hydroxy acyclic acid is from about 1.5 to about 6.5 ounces per liter of water.

12. The method of claim 11, wherein the amount of said hydroxy acyclic acid is from about 1.5 to about 2.5 ounces per liter of water.

13. The method of claim 8, wherein the amount of said surfactant is from about 1 to about 10 ml per liter of water.

14. The method of claim 13, wherein the amount of said surfactant is from about 4 to about 6 ml per liter of water.

15. A method of repelling insects from human skin comprising applying to said human skin an environmentally safe insecticide which is non-toxic to vertebrates and which consists essentially of an hydroxy acyclic acid, an ionic or non-ionic surfactant, and water, the amount of said hydroxy acyclic acid being up to about 10.5 ounces per liter of water, the amount of said surfactant being up to about 60 ml per liter of water, said hydroxy acylic acid being selected from the group consisting of citric, lactic, tartaric, malic, glycolic, tannic and ascorbic acids, said surfactant being selected from the group consisting of:

(a) alcohols;

(b) alkanolamides;

(c) alkoxylated derivatives of alcohols, alkyl phenols, amines, amides, fatty acids, fatty esters and oils;

(d) amine acetates and oxides;

(e) aryl, alkyl, aralkyl and alkaryl sulfonates and sulfates;

(f) betaine derivatives;

(g) carboxylated alcohol ethoxylates;

(h) esters of fatty acids, glycols, glycerols, sucrose, glucose and phosporic acid;

(i) fluorcarbon-based surfactants;

(j) imidazolines, imadazolines and other heterocylic surfactants;

(k) isethionates;

(l) lanolin-based derivatives;

(m) lecithin and lecithin derivatives;

(n) lignin and lignin derivatives;

(o) polysaccharides, polyacrylates, polyacrylamides, and other polymeric and block polymeric surfactants;

(p) protein-based surfactants;

(q) quaternary surfactants;

(r) sarcosine derivatives;

(s) silicone-based surfactants;

(t) soaps;

(u) sorbitan derivatives;

(v) sulfates and sulfonates of amines, amides, olefins, petroleum, oils, fatty acids, fatty esters, ethoxylated alcohols and ethoxylated alkyl phenols;

(w) sulfosuccinates and sulfosuccinamates;

(x) taurates; and (y) thio, mercapto and phosphorous derivatives.

16. The method of claim 15, wherein said hydroxy acyclic acid is citric acid.

17. The method of claim 15, wherein said surfactant is selected from the group consisting of alkaryl polyethylene glycols, alkyl polyethylene glycols, salts of dodecylated oxydibenzene disulfonate, ethoxylated nonylphenol surfactants, aliphatic polyoxyethylene ether surfactants, polyoxyethylene alkyl ether surfactants, and castor oil derivatives.

18. The method of claim 15, wherein the amount of said hydroxy acyclic acid is from about 1.5 to about 6.5 ounces per liter of water.

19. The method of claim 18, wherein the amount of said hydroxy acyclic acid is from about 1.5 to about 2.5 ounces per liter of water.

20. The method of claim 15, wherein the amount of said surfactant is from about 1 to about 10 ml per liter of water.

21. The method of claim 20, wherein the amount of said surfactant is from about 4 to about 6 ml per liter of water.

\* \* \* \* \*